United States Patent [19]

Hollub

[11] Patent Number: 5,676,141
[45] Date of Patent: Oct. 14, 1997

[54] ELECTRONIC PROCESSOR FOR PULSE OXIMETERS

[75] Inventor: Seth D. Hollub, Overland Park, Kans.

[73] Assignee: Nellcor Puritan Bennett Incorporated

[21] Appl. No.: 525,591

[22] PCT Filed: Mar. 31, 1997

[86] PCT No.: PCT/US94/03546

§ 371 Date: Sep. 19, 1995

§ 102(e) Date: Sep. 19, 1995

[87] PCT Pub. No.: WO94/22362

PCT Pub. Date: Oct. 13, 1994

Related U.S. Application Data

[63] Continuation-in-part of Ser. No. 40,839, Mar. 31, 1993, Pat. No. 5,348,004.

[51] Int. Cl.⁶ ............................................. A61B 5/00
[52] U.S. Cl. ................................. 128/633; 356/41
[58] Field of Search ........................ 128/633, 664, 128/665, 666; 356/41

[56] References Cited

U.S. PATENT DOCUMENTS

| | | |
|---|---|---|
| 2,706,927 | 4/1955 | Wood . |
| 4,086,915 | 5/1978 | Kofsky et al. . |
| 4,266,554 | 5/1981 | Hamaguri ........................ 128/633 |
| 4,394,572 | 7/1983 | Wilber . |
| 4,407,290 | 10/1983 | Wilber . |
| 4,603,700 | 8/1986 | Nichols et al. . |
| 4,653,498 | 3/1987 | New, Jr. et al. . |
| 4,759,369 | 7/1988 | Taylor . |
| 4,781,195 | 11/1988 | Martin . |
| 4,816,996 | 3/1989 | Hill et al. . |
| 4,819,752 | 4/1989 | Zelin . |
| 4,846,183 | 7/1989 | Martin . |
| 4,927,264 | 5/1990 | Shiga et al. . |
| 4,958,277 | 9/1990 | Hill et al. . |
| 5,190,038 | 3/1993 | Polson et al. . |
| 5,351,685 | 10/1994 | Potratz ........................ 128/633 |
| 5,385,143 | 1/1995 | Aoyagi ........................ 128/633 |

FOREIGN PATENT DOCUMENTS

| | | |
|---|---|---|
| 0 261 789 | 3/1988 | European Pat. Off. . |
| 0 497 021 | 8/1992 | European Pat. Off. . |

*Primary Examiner*—Lee S. Cohen
*Assistant Examiner*—Eric F. Winakur
*Attorney, Agent, or Firm*—Townsend and Townsend and Crew

[57] ABSTRACT

An apparatus for measuring the concentration of blood constituents in which the architecture of the electronic processor reduces the amount of controller processing time required for tasks such as data acquisition and generation of system control signals. A demodulator is coupled to a probe for converting a first electrical signal to digital data. An interface is coupled to the demodulator for receiving the digital data and generating interrupts when a first amount of the digital data has been received. A buffer memory is coupled to the interface for storing the digital data. A controller having a controller memory (in specific embodiments, a CPU having a CPU memory) is also coupled to the buffer memory. The controller transfers the digital data from the buffer memory to the controller memory in response to the interrupts. The controller then processes the digital data to calculate the blood oxygen concentration.

13 Claims, 5 Drawing Sheets

ELECTRONIC PROCESSOR FOR PULSE OXIMETERS

REFERENCE TO RELATED APPLICATION

This application is a continuation-in-part of commonly assigned, U.S. patent application Ser. No. 08/040,839 for ELECTRONIC PROCESSOR FOR PULSE OXIMETERS, filed Mar. 31, 1993, now U.S. Pat. No. 5,348,004, the entire specification of which is incorporated herein by reference.

BACKGROUND OF THE INVENTION

The present invention relates to a method and apparatus for making in vivo measurements of blood constituent concentrations. More specifically, a method and apparatus are described wherein hemoglobin oxygen saturation may be measured using a pulse oximeter which directs light of two or more wavelengths into living tissue and then measures the attenuation of the resultant absorbed and scattered light to determine the level of hemoglobin oxygen saturation.

It is well known that hemoglobin oxygen saturation, i.e., blood oxygenation level, can be determined by measuring the attenuation of light energy when passed through a blood sample, either in vivo or in vitro. In the bloodstream, hemoglobin loosely combines with oxygen to form oxyhemoglobin in order to transport oxygen to various body tissues where it then can be released. In vivo optical measurement of blood oxygenation level relies on the fact that, because the light absorption properties of hemoglobin and oxyhemoglobin differ, the degree to which a given blood sample attenuates light energy is directly related to the concentration of oxygen in the sample. For example, hemoglobin transmits considerably less visible red light (i.e., light having wavelengths from 620–720 nanometers (nm)) than does oxyhemoglobin. Therefore, blood with high oxygen concentrations will transmit more visible red light than will blood with low oxygen concentrations.

To provide sufficient warning of the onset of hypoxemia, a pulse oximeter must be capable of accurate and continuous real-time measurement of patient hemoglobin oxygen saturation. Oximeters have been developed which employ pulsed light sources in combination with photosensors to measure light intensities transmitted through patient tissue. Light emitting diodes (LEDs) are often used for light sources to produce, for example, visible red light and infrared radiation. In some devices, the LEDs are serially pulsed to produce an interleaved signal stream which is detected by a photosensor. The signal stream might consist of visible red light, infrared radiation, and ambient radiation interleaved in any desired manner. Such oximeters usually include a photoelectric probe and an electronic processor. The photoelectric probe, which houses the light sources and the photosensors, is positioned on a patient so that light can either be directed through the tissue (forward scattering), or reflected from the tissue (back scattering), before being detected by the photosensors. The photoelectric probe is typically mounted on the patient's finger or ear.

An electronic processor is used in conjunction with the photoelectric probe for controlling power to the light sources, measuring the amplitude of light signals from the photosensor, determining the degree to which light is attenuated by the tissue, and providing readouts of blood oxygenation levels. A pulse oximeter of this general type is disclosed in commonly assigned U.S. Pat. No. 4,621,643 to New, Jr., et al., the entire specification of which is incorporated herein by reference.

For effective, continuous, real-time monitoring of blood oxygenation levels, the operation of a pulse oximeter must be as automated as possible. For example, during surgery anesthesiologists need current, accurate, in vivo information on oxygenation levels over an extended period of time. In such situations, it is preferable that this information be available with little or no need for manual adjustment of oximeter equipment so that attention is not diverted from higher priority tasks.

Automated operation of pulse oximeters has been achieved through the use of controllers and control circuitry such as embodied in, for example, a central processing unit (CPU). CPUs have not only been used for the calculation and display of blood oxygenation levels, but also for a variety of other tasks, including data acquisition, adjustment of transmitted light intensity levels, controlling the chopping rate of the LEDs, adjustment of circuitry gains for measuring light intensities, and control of sample-and-hold (s/h) circuits and analog-to-digital (a/d) converters. Each of these tasks consumes valuable CPU processing time, therefore reducing the amount of time available for processing incoming data and calculating blood oxygenation levels. For example, the CPU is typically interrupted each chop cycle for controlling the LED drive circuits, the chopping rate usually being five to ten times greater than the ON/OFF rate of the LEDs. A chop cycle comprises an "on" period for each LED and at least one "dark" period in which none of the LEDs is transmitting energy.

In addition, the control of s/h and a/d circuitry, critical to the accuracy of a pulse oximeter, consumes a considerable amount of CPU processing time, some a/d circuits requiring interrupts at a rate which far exceeds the chop frequency. These circuits must also frequently be adjusted to cover the wide dynamic range of light signals from the photoelectric probe. The sample rates of these circuits are also adjusted to optimize the digitizing of measured light signals for subsequent CPU processing. Light source intensity and input amplifier gain may also be adjusted to assist s/h and a/d circuitry in covering the dynamic range of the light signals. Unfortunately, patient motion is an unavoidable occurrence which often necessitates frequent circuit adjustments.

Figure 1:
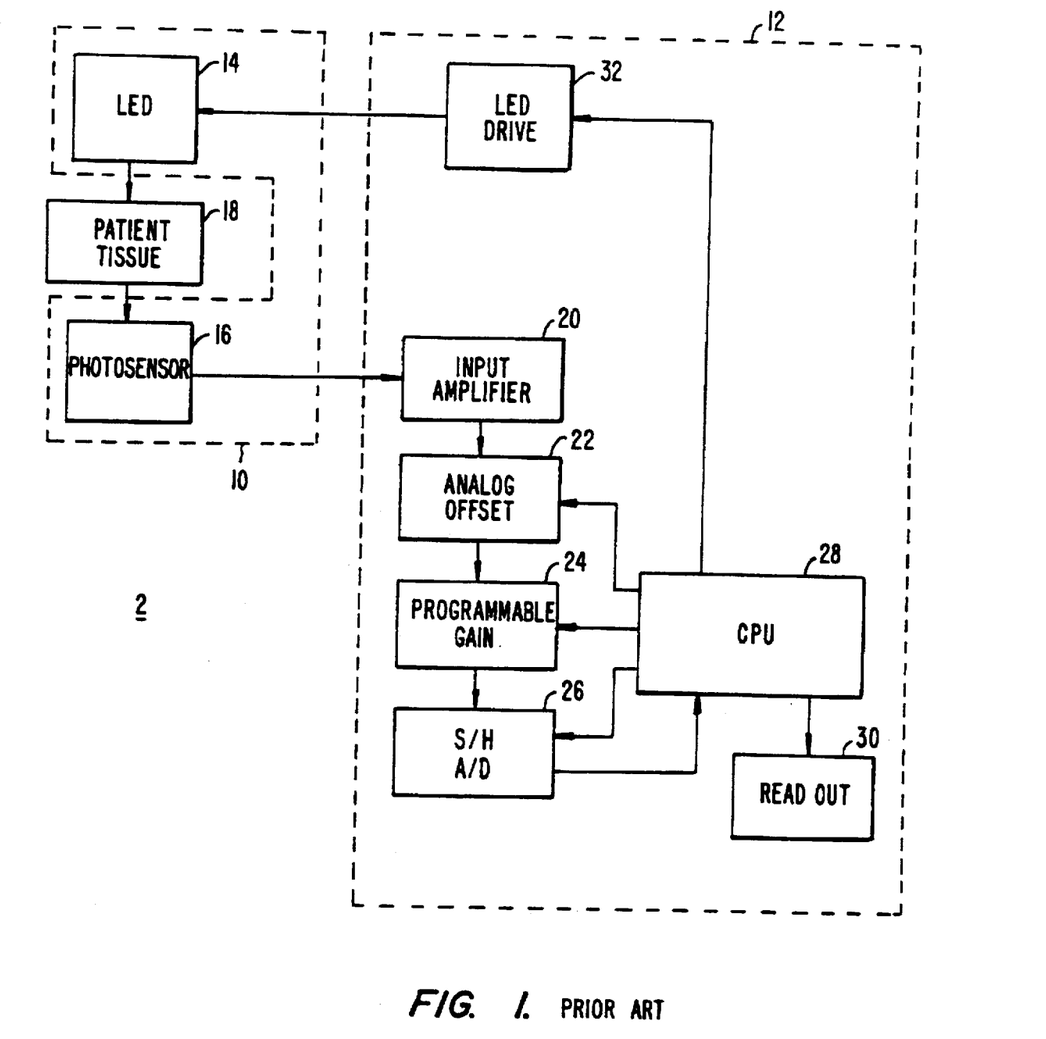
FIG. 1 is a block diagram of a pulse oximeter designed according to the prior art.

FIG. 1 is a block diagram of a pulse oximeter 2 designed according to the prior art. Pulse oximeter 2 includes a photoelectric probe 10 and an electronic processor 12. Photoelectric probe 10 includes one or more LEDs 14 and a photosensor 16. Corresponding components are similarly designated throughout the various figures.

Light from LEDs 14 passes into patient tissue 18, and after being transmitted through or reflected from tissue 18, the light is received by photosensor 16. Photosensor 16 converts the received energy into an electrical signal which is then fed to input amplifier 20, typically a fixed gain amplifier. The electrical signal is amplified thereby to provide sufficient signal amplitude for processing by subsequent circuitry. Amplifier 20 also buffers the processed signals. From amplifier 20 the signal is provided to an analog offset circuit 22 which controls the signal polarity and optionally adjusts the signal amplitude as required. The signal amplitude is additionally adjusted by programmable gain circuitry 24. These amplitude adjustments are made before the signal is processed by s/h and a/d circuitry 26 to ensure that the signal amplitude is within the limited dynamic ranges of circuits 26. If the incoming signal exceeds the dynamic ranges of these devices, signal clipping occurs, thereby providing inaccurate data to CPU 28. This ultimately results in errors in the calculation of blood oxygenation levels displayed on read-out 30.

In making the above-described amplitude adjustments, CPU 28 compares the amplitudes of the light signal to the dynamic ranges of the s/h and a/d circuits 26. When the amplitude approaches the limits of these ranges, CPU 28 adjusts several parameters to constrain the light signal amplitudes within them. For example, CPU 28 may adjust the power provided from LED drive circuit 32 to LEDs 14. CPU 28 also may adjust the gains for the analog offset circuit 22 and programmable gain circuit 24, respectively. Finally, CPU 28 may adjust the rates of signal processing for s/h and a/d circuits 26 themselves.

All of the tasks typically performed by a CPU in a pulse oximeter, including those described above, consume valuable CPU processing time and capacity. The increased use of the CPU for automated monitoring and adjustment of oximeter circuitry has resulted in an undesirable degradation in real-time performance, and a decrease in the time available for the extended calculations which are necessary for improvements in accuracy. Thus, there is a need for a pulse oximeter design in which the consumption of CPU processing time by these tasks is reduced.

SUMMARY OF THE INVENTION

According to the invention, a method and apparatus for measuring the concentration of blood constituents is provided in which the architecture of the electronic processor reduces the amount of CPU processing time required for tasks such as data acquisition and generation of system control signals. In contrast to the designs described above in which a substantial amount of CPU processing time is consumed by data acquisition and automated circuit adjustment, the invention employs autonomous circuitry, separate from the CPU, to perform these functions.

According to a preferred embodiment, a serial interface module (queued serial module) is used for data acquisition, and a control signal module (general purpose timer) is used for generation of various LED drive circuit, analog, and digital control signals, thereby allowing the CPU to focus on other tasks, including real-time processing of measured light signals, and extended calculations for improved accuracy. A reduction in CPU processing time is also realized through the use of wide range a/d converters which eliminate the need for the CPU to constantly adjust circuit parameters to account for limited dynamic range.

According to one embodiment, an apparatus for estimating arterial oxygen concentration using a first electrical signal generated by a probe is provided. A demodulator is coupled to the probe for converting the first electrical signal to digital data. A controller (in specific embodiments a CPU) is coupled to the demodulator for processing the digital data to determine the arterial oxygen concentration. A control signal generator is coupled to the controller as well as to a drive circuit for driving a source of electromagnetic radiation in the probe. The control signal generator is for generating a drive signal for the drive circuit, and optionally input amplifier gain. The control signal generator does this without intervention by the controller after the control signal generator is first initialized by the controller. This feature eliminates the need for the controller to manipulate the LED drive or the input amplifier gain.

According to a second embodiment, a demodulator is coupled to the probe for converting the first electrical signal to digital data. An interface is coupled to the demodulator for receiving the digital data and generating interrupts when a first amount of the digital data has been received. A buffer memory is coupled to the interface for storing the digital data. A controller having a controller memory (in specific embodiments, a CPU having a CPU memory) is also coupled to the buffer memory. The controller transfers the digital data from the buffer memory to the controller memory in response to the interrupts. The controller then processes the digital data to calculate the arterial oxygen concentration. In a specific embodiment, the probe includes a source of electromagnetic radiation, and a detector for detecting a portion of the electromagnetic radiation from the source, and converting it to the first electrical signal.

According to a third embodiment, a method and an apparatus for estimating arterial oxygen concentration are provided. In this embodiment, the first electrical signal comprises a plurality of phases, each of which corresponds to a period during which a particular type of electromagnetic radiation is being received by a sensor in the probe. Each phase of the first electrical signal is sampled a plurality of times. The samples from each phase are then converted to first digital data. The first digital data from each phase are then averaged, thereby generating average digital data for each phase. This increases the signal-to-noise ratio for the data for each phase. Second digital data for each phase is then generated from the average digital data using appropriate filtering techniques, such as median filtering and/or averaging filtering for example. The arterial oxygen concentration is then calculated by analyzing the second digital data.

According to a fourth embodiment an analog-to-digital converter for converting the first electrical signal to the digital data is coupled to the probe and to the controller. The analog-to-digital converter has a dynamic range, and the first electrical signal has an amplitude range. The dynamic range of the analog-to-digital converter is sufficient to cover the amplitude range of the first electrical signal, thereby eliminating the need for the controller to manipulate the amplitude range of the first electrical signal by, for example, adjusting the LED drive and/or the input amplifier gain.

In another embodiment, the invention includes a control signal module coupled to the CPU and the source of electromagnetic radiation. The control signal module generates a chop drive signal for driving the source of electromagnetic radiation, and a gating signal for gating the first electrical signal, thereby facilitating synchronous detection. The drive and gating signals are generated without intervention by the CPU once the control signal module has been initialized by the CPU.

According to another embodiment, a demodulator is provided as an analog switch. Detected light signal waveforms are fed from the photoelectric probe photosensor into temporally controlled analog switches for synchronous detection. One of the outputs from each analog switch is connected to ground. Each analog switch is followed by a low-pass filter, and then with a wide range a/d converter. Outputs from these a/d converters interface with the serial interface module. This module is used to acquire data to be provided to the CPU. The control signal module provides control signals to the LED drive circuitry as well as to the analog switches to facilitate synchronous detection as described.

In a further embodiment, the serial interface, the buffer memory, the CPU, and the control signal module are part of one integrated circuit.

A further understanding of the nature and advantages of the present invention may be realized by reference to the remaining portions of the specification and the drawings.

DESCRIPTION OF SPECIFIC EMBODIMENTS

Figure 2:
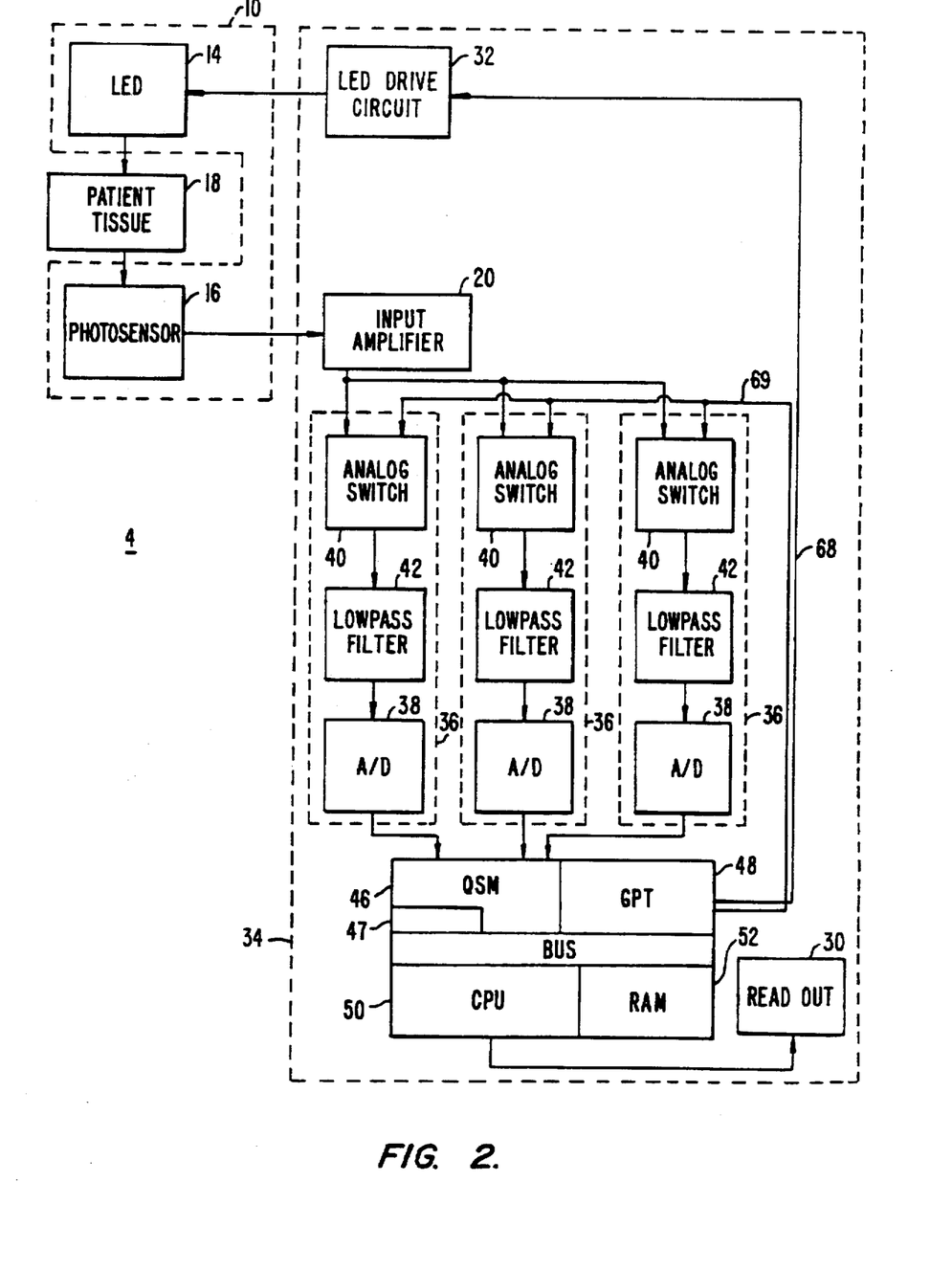
FIG. 2 is a block diagram of a pulse oximeter including a demodulator, and processing and control circuitry designed according to one embodiment of the invention.

According to the invention, and with reference to FIG. 2, general purpose timer (GPT) module 48 provides control signals to drive the LEDs and gate the incoming photosensor signals to provide for synchronous detection after initialization of the timing of the LED drive, analog, and digital circuits by the CPU. If CPU 50 is required to control the timing of the LED drive, analog, and digital circuits, the acquisition of serial digital data consumes as much as 40% of CPU capacity. According to the invention, GPT 48 sends a control signal 68 to a fixed or variable power output LED driver circuit 32. The parameters of control signal 68 are initialized by CPU 50, but are thereafter sustained by GPT 48. A control signal 69 from GPT 48 is also used for controlling operation of analog switches 40 to implement synchronous detection of each signal type to be processed, i.e., visible, infrared, and noise. Control signal 69 is used to enable one of oversampling demodulators 36 at a time for transmission of a particular signal type. This may be accomplished with one signal line by the use of, for example, a two-bit binary decoder which selects the appropriate demodulator 36 based upon an encoded signal on line 69. It will be understood that any number of oversampling demodulators 36 can be used depending on the number of signal types to be processed. Furthermore, a single oversampling demodulator 36 may be used to process multiple signal types through proper application of the timing signal from GPT 48. Without GPT 48, special purpose hardware or software would be required to perform the LED drive and photosensor gating functions. If a software implementation were used, another substantial fraction of CPU capacity would be consumed.

According to a preferred embodiment, a wide range a/d converter is utilized, such as the AD7710 converter from Analog Devices, Inc. Using 60 sample per second/19–24 bit conversion capacities, this new monolithic a/d converter is capable of generating serial digital data having a resolution of at least 18 bits, and can accurately sample the entire dynamic range of an oximeter photosensor output. In contrast, however, reasonably priced, currently available s/h devices only have comparable capacities up to approximately 16 bits which necessitates intensive use of CPU processing capacity for circuit parameter adjustment. Hence, one embodiment of the present invention not only eliminates the use of CPU processing capacity for circuit parameter adjustments, but also the need for s/h circuits.

FIG. 2 is a block diagram of one embodiment of a pulse oximeter 4 designed according to the present invention.

Pulse oximeter 4 employs a photoelectric probe 10 which includes LEDs 14 and photosensor 16. Photoelectric probe 10 operates as described above with reference to FIG. 1. Input amplifier 20 and readout 30 also operate as described above.

Photosensor 16 provides an electrical signal representative of detected light to electronic processor 34. The signal is then processed by input amplifier 20 which typically has a fixed transconductance gain. As described above, input amplifier 20 provides sufficient signal amplitude for processing by subsequent circuitry and also buffers processed signals. After amplification by input amplifier 20, the signal is provided to oversampling demodulators 36. Included in each oversampling demodulator 36 is a wide range a/d converter 38 which has a conversion resolution of 19–24 bits. A/d converters 38 may be, for example, AD7710 circuits from Analog Devices, Inc. A/d converters 38 are used in demodulators 36 without s/h circuits or any adjustment of circuit gains. Demodulators 36 also include an analog switch 40 for signal processing, which may be an ADG221 from Analog Devices, Inc. Switching rates for analog switch 40 should be about ten times greater than LED 14 cycle rates. For example, if LED 14 is operating at a frequency of 1.6 kHz, the switching rates for analog switches 40 should be at least 16 kHz. Each analog switch 40 intermittently switches the output signal from amplifier 20 between ground and a channel that includes low-pass filter 42 for noise reduction. A filter cutoff frequency of about 15 Hz for low-pass filter 42 has been found appropriate for rejecting noise while still passing signals representative of blood oxygenation levels.

Figure 3:
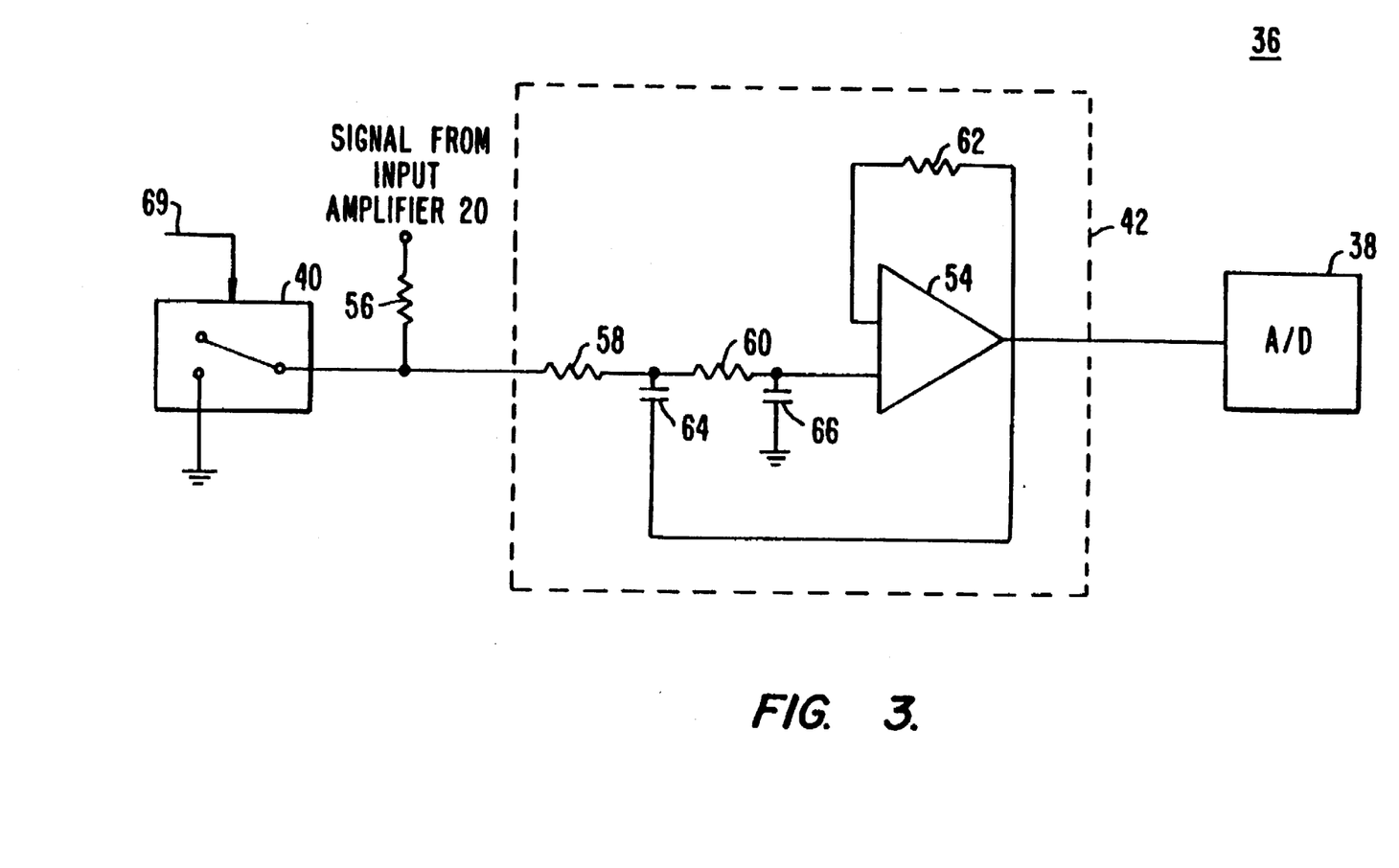
FIG. 3 is a schematic diagram of a demodulator designed according to one embodiment of the invention.

FIG. 3 is a circuit diagram of one embodiment of an oversampling demodulator 36 designed according to the invention. Analog switch 40 may be an ADG221, operational amplifier 54 may be a TLOS4 from Analog Devices, Inc., and a/d converter 38 may be an AD7710. Typical values for resistors and capacitors in oversampling demodulator 36 as shown in FIG. 3 are set out in Table I.

TABLE I

| Resistor | Value | Capacitor | Value |
| --- | --- | --- | --- |
| 56 | 15 kΩ | 64 | 0.01 μF |
| 58 | 11.5 kΩ | 66 | 0.01 μF |
| 60 | 10 kΩ | | |
| 62 | 10 kΩ | | |

In a specific embodiment, three demodulators are coupled in parallel between the probe and the serial interface. One demodulator is for generating serial data when the red LED is transmitting. A second is for generating serial data when the infrared LED is transmitting, and a third is for generating serial data when neither the red nor the infrared LEDs are transmitting.

The output from photosensor 16 is typically a current signal. Input amplifier 20 may be operated to convert this to a voltage signal. Analog switch 40 (as shown in FIG. 3) provides switching of the input signal between ground and low-pass filter 42 which is operated in a high impedance voltage mode. This processing, in combination with a 50–60 Hz sample rate for wide range a/d converters 38, permits coverage of the entire range of input signal frequencies expected for blood oxygenation measurements. A/d converters 38 may also include internal digital low-pass filtering. In such cases, low-pass filters 42 act as anti-aliasing filters for a/d converters 38.

Some of the advantages of oversampling demodulators designed according to the invention are: i) significant noise rejection due to the fact that the high frequency switching rates are far from power line harmonics; ii) the elimination of sample and hold circuits which in turn eliminates the error introduced by sample and hold circuits; and iii) the greater dynamic range of wide range a/d converters.

Referring back to FIG. 2, serial digital data from a/d converters 38 are provided to queued serial module (QSM) 46. QSM 46 has an input buffer memory 47 in which it can store up to 16 bytes of incoming serial digital data. When input buffer 47 is full, QSM 46 generates an interrupt, in response to which, CPU 50 quickly transfers the buffered data from input buffer 47 to RAM 52. QSM 46 continues to read data from a/d converters 38. QSM 46 is initialized by CPU 50 to automatically read the incoming data stream from a/d converters 38, but operates independently thereafter. During operation of pulse oximeter 4, QSM 46 can receive up to 16 bytes of serial data without intervention by CPU 50. Thus, CPU 50 is interrupted only once for every 16 bytes of data received, rather than once for every byte. This allows CPU 50 to spend more of its time running sophisticated algorithms. Additionally, because QSM 46 handles synchronization and status lines without CPU intervention, the actions required by CPU 50 to transfer 16 bytes of data are simpler than those which would be required if CPU 50 had to transfer each byte directly from a/d converters 38.

It will be understood that any of the above-described schemes for minimizing the consumption of CPU processing time may be used independently, or in combination with any other scheme without departing from the scope of the invention. For example, a reduction in the demand for CPU processing time may be effected with QSM 46 and GPT 48 without the use of wide range a/d converters 38. In such a case, a/d converters with smaller ranges may be employed, and CPU 50 would be required to dynamically calculate and set power levels and circuit gains to ensure that signal clipping does not occur.

Figure 4:
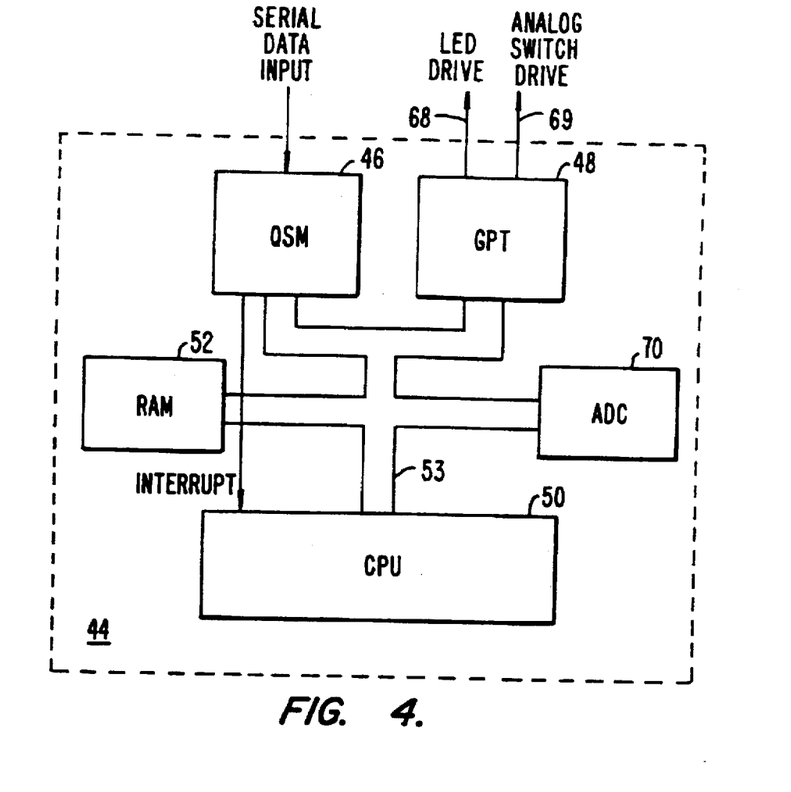
FIG. 4 is an internal block diagram of a microcontroller employed in a specific embodiment of the invention.

In a specific embodiment of pulse oximeter 4, QSM 46, GPT 48, RAM 52, and CPU 50 are all included as part of one integrated circuit, shown in FIG. 4 as microcontroller 44. QSM 46 and GPT 48 communicate with CPU 50 via internal bus 53. Microcontroller 44 may be an MC68HC16 microcontroller from Motorola. Microcontroller 44 may also contain an internal a/d converter 70 which, due to its limited dynamic range, is not suitable for use in some embodiments of the invention. As described above, however, in other embodiments, the internal a/d converter 70 may be used in place of wide range a/d converters 38. In such an embodiment, CPU 50 would be required to dynamically calculate and set power levels and circuit gains to ensure that signal clipping does not occur. However, the savings in CPU processing time realized by the use of QSM 46 and GPT 48 will still be achieved.

Figure 5:
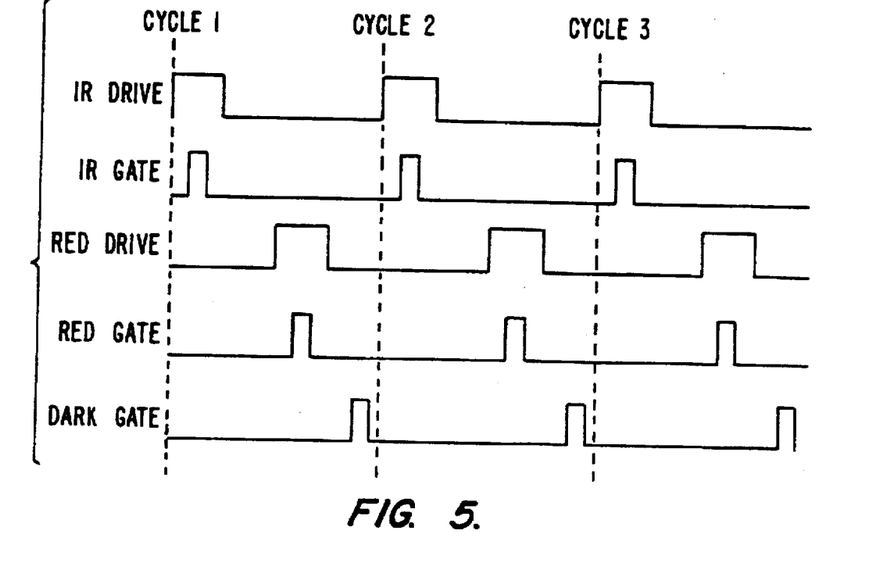
FIG. 5 is a timing diagram showing the relationship between the LED drive and gating signals.
Figure 6:
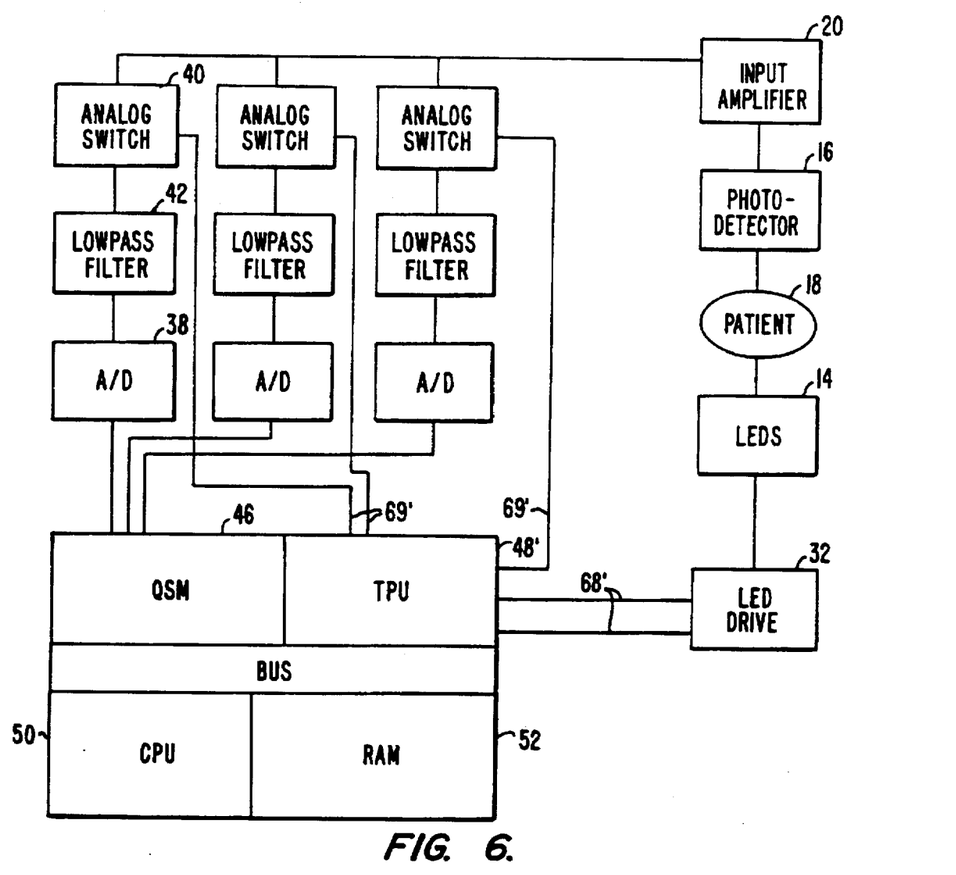
FIG. 6 is a block diagram of a pulse oximetry system designed according to another embodiment of the present invention.

In another embodiment, microcontroller 44 may comprise a Motorola 68332. The 68332 is similar to the 68HC16 except that it has a time processing unit (TPU) instead of a GPT. The TPU has more control signal lines than the GPT, thus allowing for more sophisticated driving and gating schemes. For example, as opposed to an embodiment employing a GPT in which the analog switch gating signal is synchronous with the LED drive, an embodiment employing a TPU may gate each of the analog switches independently as shown in FIG. 5. As shown in the figure, the gate for each LED occurs some time after the drive signal for that LED is asserted, and turns off some time before the drive turns off. This allows the photodetector and the input amplifier to settle before a data point is taken. The block diagram of FIG. 6 illustrates such an embodiment, which is only slightly modified from the embodiment of FIG. 2. GPT 48 is replaced by TPU 48' and control signal lines 68 and 69 are replaced by lines 68' and 69'.

Another embodiment of the invention will be described with reference to the oximetry system 100 of FIG. 7. This embodiment includes four basic elements. A gain stage 102 is an op-amp based current-to-voltage converter. In a preferred embodiment, the a/d converter 104 is a 12-14 bit, monolithic, high speed a/d converter running at 500,000 samples per second. A programmable gate array (PGA) 106 is a configurable logic device which performs several functions, including controlling LED drive 110, reading a/d converter 104, and downsampling the data from a/d converter 104. A controller 108 initiates the operation of PGA 106 and runs high level oximetry calculations using the downsampled data from PGA 106.

Figure 7:
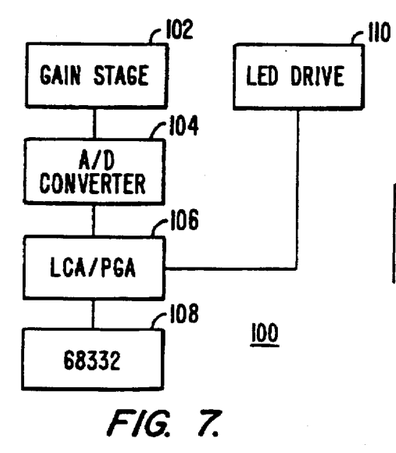
FIG. 7 is a block diagram of a pulse oximetry system designed according to still another embodiment of the present invention.

The system of FIG. 7 is designed around the concept of oversampling. Signals are digitized at a substantially higher speed and a lower resolution than the ultimate data acquisition rate, and then averaged to produce a higher signal-to-noise ratio. As used with reference to the embodiments described with reference to FIGS. 2–6, the term "oversampling" refers to the relationship between the LED drive rate (i.e., the chop rate) and the ultimate digital data acquisition rate (57.1 samples per second per wavelength in specific embodiments of the invention). With respect to the embodiment of FIG. 7, "oversampling" is used to refer to the relationship between the a/d converter sample rate and the LED drive rate (i.e., the chop rate).

Figure 8:
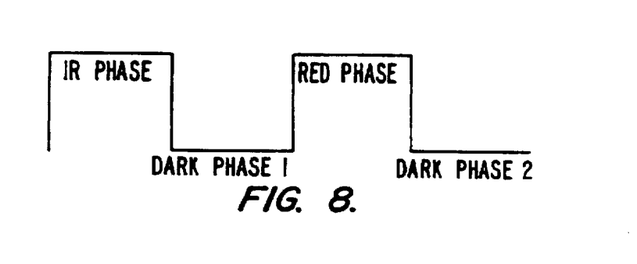
FIG. 8 is a representation of a "chop cycle" according to a specific embodiment of the present invention.

According to the embodiment of FIG. 7, a/d converter 104 is a single a/d converter operating at a rate significantly higher than the rates at which the LEDs are driven so that the single a/d converter can sample each of the "phases" in a "chop cycle" numerous times, i.e., hundreds or thousands of times per phase. A typical chop cycle for this embodiment is shown in FIG. 8. The first portion of the waveform, the infrared phase, corresponds to the period of time during which the infrared LED is "on". The second and fourth portions of the waveform, "dark" phases 1 and 2, correspond to the period of time during which neither of the LEDs is "on". The third portion of the waveform, the red phase, corresponds to the period of time during which the red LED is "on". Each phase of the chop cycle is sampled a number of times by a/d converter 104. PGA 106 averages the samples for each phase, yielding a high signal-to-noise ratio for each phase, and then subtracts the values obtained for the dark phases from their preceding LED phases to yield a signal level estimate for each LED phase which is free of ambient light.

For example, if an LED chop rate of 1000 cycles per second and an a/d sample rate of 500,000 samples per second are chosen, the oversampling ratio is 500. This means that there are 125 samples per phase. Under normal circumstances, i.e., zero mean noise, the signal-to-noise improvement derived from oversampling for a particular phase is the square root of the number of samples per phase, or in this case a factor of ~11. This translates to a signal-to-noise improvement of approximately 20 dB; i.e., 20 log(sqrt(125)). Additional improvements in signal-to-noise ratio may be derived from the fact that the LED chop rate is much greater than the rate at which data is delivered to the CPU. For a four phase system at 1000 cycles per second, there are 250 samples for each of the two LEDs in one second. If the typical CPU data rate of 57.1 samples per second is used, an additional improvement of approximately 6 dB may be achieved; (i.e., 20 log(sqrt(250/57.1))=6.41). If this improvement is applied to a typical 14 bit a/d converter operating at 500,000 samples per second, which typically exhibits a signal-to-noise ratio of 72 dB, a signal-to-noise ratio of 98 dB can be achieved.

Due to processing rate limitations, the ultimate desired data rate is significantly lower than the a/d sample rate, or even the LED chop rate. PGA 106 interfaces with a/d converter 104, receives the samples at the a/d sample rate and transmits data for use by controller 108 at the desired data rate. In one embodiment, the output from PGA 106 are 8-bit parallel words at 57.1 samples per second. In another embodiment, the output of PGA 106 comprises serially coded words at the same data rate. In addition, PGA 106 generates LED drive signals. After controller 108 writes an LED clock rate to a register in PGA 106, PGA 106 controls the LED drive without further intervention by controller 108. PGA 106 also generates a/d conversion clocks, and interface timing based on the LED clock rate.

While the invention has been particularly shown and described with reference to specific embodiments thereof, it will be understood by those skilled in the art that the foregoing and other changes in the form and details may be made therein without departing from the spirit or scope of the invention.

What is claimed is:

1. An apparatus for calculating arterial oxygen concentration using an electrical signal generated by a probe, comprising:

at least one demodulator coupled to the probe for converting the electrical signal to digital data;

a queued serial module coupled to said demodulator and configured to generate an interrupt signal only after multiple bytes of digital data have been received from said demodulator;

a controller coupled to said queued serial module to receive said multiple bytes of digital data in response to said interrupt signal and for processing the digital data to calculate the arterial oxygen concentration; and a control signal generator coupled to the controller and a drive circuit for driving a source of electromagnetic radiation in the probe, the control signal generator for generating a drive signal for the drive circuit, the drive signal being generated without intervention by the controller after the control signal generator is initialized by the controller;

wherein the control signal generator also generates a gating signal for gating the electrical signal to facilitate synchronous detection, the gating signal being generated without intervention by the controller after the control signal generator is initialized by the controller.

2. The apparatus of claim 1 wherein the electrical signal comprises a plurality of phases, each phase corresponding to a period during which a particular type of electromagnetic radiation is being received by a sensor in the probe, and wherein the at least one demodulator comprises:

at least one analog-to-digital converter for receiving the electrical signal and sampling each phase a plurality of times, thereby generating a plurality of samples for each phase, the at least one analog-to-digital converter converting the samples from each phase to first digital data; and a logic circuit coupled to the at least one analog-to-digital converter for filtering the first digital data from each phase, thereby increasing a signal-to-noise ratio, the logic circuit generating the digital data.

3. An apparatus for calculating arterial oxygen concentration using an electrical signal generated by a probe, comprising:

at least one demodulator coupled to the probe for converting the electrical signal to digital data;

a controller coupled to the at least one demodulator for processing the digital data to calculate the arterial oxygen concentration; and a control signal generator coupled to the controller and a drive circuit for driving a source of electromagnetic radiation in the probe, the control signal generator for generating a drive signal for the drive circuit, the drive signal being generated without intervention by the controller after the control signal generator is initialized by the controller;

wherein the control signal generator also generates a gating signal for gating the electrical signal to facilitate synchronous detection, the gating signal being generated without intervention by the controller after the control signal generator is initialized by the controller;

wherein the at least one demodulator comprises an analog-to-digital converter having a dynamic range, and the electrical signal has an amplitude range, the dynamic range being sufficient to cover the amplitude range without clipping, thereby eliminating a need to manipulate the amplitude range of the electrical signal.

4. The apparatus of claim 3 wherein the analog-to-digital converter converts the electrical signal into serial digital data having a resolution of at least 18 bits.

5. An apparatus for calculating arterial oxygen concentration using a first electrical signal generated by a probe, comprising:

at least one demodulator coupled to the probe for converting the first electrical signal to digital data;

an interface coupled to the demodulator for receiving the digital data and generating interrupts when a plurality of samples of the digital data has been received;

a buffer memory coupled to the interface for storing the digital data; and a controller having a controller memory, the controller being coupled to the buffer memory, the controller transferring the digital data from the buffer memory to the controller memory in response to the interrupts, the controller for processing the digital data to calculate the arterial oxygen concentration.

6. The apparatus of claim 5, further comprising a control signal generator coupled to the controller and a drive circuit for driving a source of electromagnetic radiation in the probe, the control signal generator for generating a drive signal for the drive circuit, and for generating a gating signal for gating the first electrical signal to facilitate synchronous detection, the drive and gating signals being generated without intervention by the controller after the control signal generator is initialized by the controller.

7. The apparatus of claim 6 wherein the interface, the buffer memory, the controller, and the control signal generator are part of one integrated circuit.

8. The apparatus of claim 5 wherein the first electrical signal comprises a plurality of phases, each phase corresponding to a period during which a particular type of electromagnetic radiation is being received by a sensor in the probe, and wherein the at least one demodulator comprises:

at least one analog-to-digital converter for receiving the first electrical signal and sampling each phase a plurality of times, thereby generating a plurality of samples for each phase, the at least one analog-to-digital converter converting the samples from each phase to first digital data; and a logic circuit coupled to the at least one analog-to-digital converter for filtering the first digital data from each phase, thereby increasing a signal-to-noise ratio, the logic circuit generating the digital data.

9. An apparatus for calculating arterial oxygen concentration using a first electrical signal generated by a probe, comprising:

at least one demodulator coupled to the probe for converting the first electrical signal to digital data, said demodulator including an analog switch coupled to the probe for intermittently switching the first electrical signal to ground, thereby generating a switched electrical signal, a filter coupled to the analog switch for filtering the switched electrical signal, thereby generating a filtered electrical signal, and an analog-to-digital converter coupled to the filter for converting the filtered electrical signal to the serial digital data;

an interface coupled to the demodulator for receiving the digital data and generating interrupts when a first amount of the digital data has been received;

a buffer memory coupled to the interface for storing the digital data; and a controller having a controller memory, the controller being coupled to the buffer memory, the controller transferring the digital data from the buffer memory to the controller memory in response to the interrupts, the controller for processing the digital data to calculate the arterial oxygen concentration.

10. A method for calculating arterial oxygen concentration using a first electrical signal generated by a probe, the first electrical signal comprising a plurality of phases, each phase corresponding to a period during which a particular type of electromagnetic radiation is being received by a sensor in the probe, the method comprising the steps of:

sampling each phase of the first electrical signal a plurality of times, thereby generating a plurality of samples for each phase;

converting the samples from each phase to first digital data;

averaging the first digital data from each phase, thereby generating average digital data for each phase, and increasing a signal-to-noise ratio for each phase;

generating second digital data for each phase from the average digital data; and calculating the arterial oxygen concentration by analyzing the second digital data.

11. The method of claim 10 wherein at least three phases of at least one electrical signal cycle comprise a first phase corresponding to a first electromagnetic radiation, a second phase corresponding to ambient background radiation, and a third phase corresponding to a second electromagnetic radiation, and wherein the step of generating second digital data comprises:

subtracting the filtered digital data for the second phase from the filtered digital data for the first phase to produce second digital data for the first phase; and subtracting the filtered digital data for the second phase from the filtered digital data for the third phase to produce second digital data for the third phase.

12. An apparatus for calculating oxygen concentration using a first electrical signal generated by a probe, the first electrical signal comprising a plurality of phases, each phase corresponding to a period during which a particular type of electromagnetic radiation is being received by a sensor in the probe, the apparatus comprising:

a demodulator for receiving the first electrical signal and sampling each phase a plurality of times, thereby generating a plurality of samples for each phase, the demodulator converting the samples from each phase to first digital data;

a logic circuit coupled to the demodulator for filtering the first digital data from each phase, thereby generating filtered digital data for each phase and increasing a signal-to-noise ratio for each phase, the logic circuit generating second digital data from the filtered digital data; and a controller coupled to the logic circuit for calculating the arterial oxygen concentration by analyzing the second digital data;

wherein at least three phases of at least one first electrical signal cycle comprise a first phase corresponding to a first electromagnetic radiation, a second phase corresponding to a second electromagnetic radiation, and a third phase corresponding to ambient background radiation, and wherein the logic circuit is for subtracting the filtered digital data for the third phase from the filtered digital data for the first phase to produce second digital data for the first phase, and subtracting the filtered digital data for the third phase from the filtered digital data for the second phase to produce second digital data for the second phase.

13. The apparatus of claim 12 wherein the demodulator comprises an analog-to-digital converter having a dynamic range, and the first electrical signal has an amplitude range, the dynamic range being sufficient to cover the amplitude range, thereby eliminating a need for the controller to manipulate the amplitude range of the first electrical signal.

* * * * *

UNITED STATES PATENT AND TRADEMARK OFFICE
CERTIFICATE OF CORRECTION

PATENT NO. : 5,676,141
DATED : October 14, 1997
INVENTOR(S) : Seth D. Hollub

It is certified that error appears in the above-identified patent and that said Letters Patent is hereby corrected as shown below:

On the title page,

[22] PCT Filed: Mar. 31, 1997 should read as follows: [22] PCT Filed: Mar. 31, 1994

Signed and Sealed this

Twentieth Day of July, 1999

Attest:

Attesting Officer

Q. TODD DICKINSON

Acting Commissioner of Patents and Trademarks